US006602517B2

(12) United States Patent
Darland et al.

(10) Patent No.: US 6,602,517 B2
(45) Date of Patent: Aug. 5, 2003

(54) DIETARY SUPPLEMENTS FOR TREATING INFLAMMATION-RELATED DISEASES

(75) Inventors: Gary K. Darland, Gig Harbor, WA (US); Daniel O. Lukaczer, Gig Harbor, WA (US); DeAnn J. Liska, Gig Harbor, WA (US); Tracey A. Irving, Gig Harbor, WA (US); Jeffrey S. Bland, Fox Island, WA (US)

(73) Assignee: Metagenics, Inc., San Clemente, CA (US)

( * ) Notice: Subject to any disclaimer, the term of this patent is extended or adjusted under 35 U.S.C. 154(b) by 0 days.

(21) Appl. No.: 09/773,280

(22) Filed: Jan. 29, 2001

(65) Prior Publication Data

US 2002/0051826 A1 May 2, 2002

Related U.S. Application Data

(62) Division of application No. 09/302,693, filed on Apr. 30, 1999, now Pat. No. 6,210,701.

(51) Int. Cl.[7] .................. A61K 47/00; A61K 39/385
(52) U.S. Cl. ..................... 424/439; 424/195.1
(58) Field of Search .................. 424/725, 750, 424/756, 439, 195.1; 514/783; 426/49

(56) References Cited

U.S. PATENT DOCUMENTS

| 4,755,504 A | * | 7/1988 | Liu |
| 4,876,096 A | * | 10/1989 | Mitchell et al. |
| 5,120,538 A | * | 6/1992 | Oei |
| 5,401,504 A | * | 3/1995 | Das et al. |
| 5,401,777 A | * | 3/1995 | Ammon et al. |
| 5,494,668 A | * | 2/1996 | Patwardhan |
| 5,858,371 A | * | 1/1999 | Singh et al. |
| 5,904,924 A | * | 5/1999 | Gaynor et al. |
| 5,952,295 A | * | 9/1999 | Arnaud-Battandier et al. |
| 6,022,558 A | * | 2/2000 | Hu et al. |
| 6,194,469 B1 | | 2/2001 | Nair et al. |

FOREIGN PATENT DOCUMENTS

| DE | 19720767 | * | 11/1998 |
| JP | 401083022 | * | 3/1989 |
| JP | 04295428 | * | 10/1992 |

* cited by examiner

*Primary Examiner*—Michael V. Meller
(74) *Attorney, Agent, or Firm*—Knobbe, Martens, Olson & Bear, LLP

(57) ABSTRACT

The present invention provides dietary supplements, medical foods and methods effective to ameliorate at least one of the symptoms, preferably all of the symptoms, of an inflammation-related disease. The dietary supplements of the present invention include rosemary, curcumin and at least one component selected from the group consisting of quercetin and rutin. The medical foods of the present invention include include rosemary and at least one component selected from the group consisting of curcumin, quercetin and rutin. The medical foods of the present invention also include macronutrients. The methods of the present invention include the step of administering to a person suffering from an inflammation-related disease an effective amount of a dietary supplement or medical food of the present invention.

7 Claims, No Drawings

DIETARY SUPPLEMENTS FOR TREATING INFLAMMATION-RELATED DISEASES

CROSS-REFERENCE TO RELATED APPLICATION

This application is a divisional of U.S. patent application Ser. No. 09/302,693 filed Apr. 30, 1999, now U.S. Pat. No. 6,210,701.

FIELD OF THE INVENTION

The present invention relates to dietary supplements and medical foods for treating inflammation-related diseases. The compositions of the present invention include rosemary.

BACKGROUND OF THE INVENTION

In 1948, the World Health Organization defined health as not only the absence of disease, but also the presence of physical, mental, and social well-being. (Constitution of the World Health Organization. In: World Health Organization, Handbook of Basic Documents. 5th ed. Geneva: Palais des Nations, 3–20 (1952)). The status of a patient's physical, mental, and social functioning is often referred to in the literature as quality-of-life and is used as a measure of health outcome. In the past 25 years, there has been a nearly exponential increase in the evaluation of quality-of-life as a technique of clinical research as a component of determining clinical benefit from an intervention protocol. For example, in 1973, only five articles listed quality-of-life as a key word in the Medline database, whereas in the subsequent four years there were successively 195, 273, 490, and 1,252 such articles. (Testa M A and Simonson D C, *N Eng J Med.* 334:835–840 (1996). In 1998, approximately 3,724 articles listed quality-of-life as a key word. Thus, the health outcome, or quality-of-life, associated with a clinical intervention has been recognized as an important tool in measuring effectiveness and costs of medical care. (Wilson I B and Cleary P D., *JAMA.,* 273:59–65 (1995)).

Extensive research has resulted in the development of instruments that measure health outcome using quality-of-life tools that follow academically well-established and statistically validated psychometric principles. (Ware J E Jr., *J Chronic Dis.,* 40:473–480 (1987); Spilker B., Quality of Life and Pharmacoeconomics in Clinical Trials, 2nd ed. Philadelphia, Pa.: Lippincott-Raven Co; 1995.) One such tool is the SF-36 (Short form-36), which has been widely used in clinical trials and in clinical practice to assess health outcome. (Clancy C M and Eisenberg J M, *Science,* 282:245–246 (1998)). The SF-36 was derived from the Medical Outcomes Study, which involved 11,336 patients from 523 different clinical sites. (Ware J E, Sherbourne C D, Davies A R. Developing and testing the MOS 20-item short-form health survey. In: Stewart A L and Ware J E, eds., Measuring functioning and well-being: The Medical Outcomes Study approach. Durham, N. C.: University Press, 277–290 (1992); Ware JE. SF-36 Health Survey: manual and interpretation guide. Boston, Mass.: Nimrod Press; 2:1–3:22 (1993)). The validity and reliability of the SF-36 has been proven in several studies in which researchers tested internal consistency, within subject reliability, and differentiation between patient populations. (McHorney C A, et al., *Medical Care,* 31:247–263 (1993); McHorney C A, et al., *Medical Care,* 30:S253–S265 (1992); Jenkinson C, et al., *Br Med J,* 306:1436–1440 (1993); Brazier J E, et al., *Br Med J* 305:160–164 (1992)). The SF-36 has been shown to predict the course of depression during a two-year study, and to be lower overall in patients who experience chronic health disorders. (Wells K B, et al., *Archives General Psychiatry,* 49:788–794 (1992); Schlenk E A, et al., *Quality of Life Res.,* 7:57–65 (1998)).

The SF-36 is a 36-item questionnaire that assesses eight dimensions of health outcome: physical functioning, role-physical, bodily pain, general health, vitality, social functioning, role-emotional, and mental health. Results from the questionnaire can be reported as a relative number on a scale of 0 to 100, in which 100 is the highest or most functional and 0 is the most compromised for that category of functioning. A summary of the meaning of high and low scores for each category is shown in Table 1.

TABLE 1

Description of Very High and Very Low Scores for the Eight Categories of the MOS SF-36 Questionnaire.

| SF-36 Category | Interpretation of a Low Score | Interpretation of a High Score |
| --- | --- | --- |
| Physical Functioning (PF) | Limited in performing all physical activities including bathing or dressing due to health | Performs all types of physical activities including the most vigorous without limitations due to health |
| Role-Physical (RP) | Problems with work or other daily activities as a result of physical health | No problems with work or other daily activities as a result of physical health |
| Bodily Pain (BP) | Very severe and extremely limiting pain | No pain or limitations due to pain |
| General Health (GH) | Evaluates personal health as poor and believes it is likely to get worse | Evaluates personal health as excellent |
| Vitality (VT) | Feels tired and worn out all of the time | Feels full of pep and energy all of the time |
| Social Functioning (SF) | Extreme and frequent interference with normal social activities due to physical or emotional problems | Performs normal social activities without interference due to physical or emotional problems |
| Role-Emotional (RE) | Problems with work or other daily activities as a result of emotional problems | No problems with work or other daily activities as a result of emotional problems |
| Mental Health (MH) | Feelings of nervousness and depression all of the time | Feels peaceful, happy, and calm all of the time |

The latter half of the twentieth century has been characterized by an increasing prevalence of chronic disorders. Indeed, seven of the ten leading causes of death in the USA are chronic in nature, accounting for 72% of the deaths from all causes. (National Center for Health Statistics. Health, United States, 1995. Hyattsville, Md.: Public Health Service, 1995.) Chronic disorders such as rheumatic disorders, chronic pain, and fatigue contribute to the 6% of the population that is impaired to some extent in the conduct of major life activities such as work, school, and self-care. (US Department of Health and Human Services, Public Health Service. Healthy People 2000: National Health Promotion and Disease Prevention Objectives. Hyattsville, Md.: Public Health Service; 1991.) Health care use also appears to be substantial for patients with chronic conditions.

In chronic conditions such as rheumatic disorders and chronic pain, biological and physiological factors have an inconsistent relationship to symptoms. (Wilson I B, Cleary P D., *JAMA,* 273:59–65 (1995)). Therefore, they are difficult to measure by laboratory values. In fact, in clinical practice, anywhere from 30% to 80% of patients who see a physician may have conditions for which no physiological or organic cause is found after routine investigation. (Wilson I B and Cleary P D, *JAMA,* 273:59–65 (1995)).

In these chronic conditions, pain and fatigue are often suffered over many years without correlation to a diagnosable or definable acute or chronic disease. Therefore, without anatomical or physical correlation, a patient's response to therapy must be monitored by measuring the level of symptoms they report over a period of time. The MOS SF-36 questionnaire is particularly suited to this type of analysis. For example, patients with chronic disorders have been reported to score lower than the norm in several categories of the MOS SF-36, including bodily pain, role-physical, role-emotional, and vitality. See, e.g., Ware J E., SF-36 Health Survey: manual and interpretation guide. Boston, Mass.: Nimrod Press; 2:1–3:22 (1993); Schlenk E A, et al., Health-related quality of life in chronic disorders: a comparison across studies using the MOS SF-36, *Quality Life Research*, 7:57–65 (1998)).

Although similarities in different categories of the MOS can be observed, data from patients who experience chronic conditions suggests that these patients may show higher variability when analyzing individual MOS categories than with the PCS and MCS summary scores. This variability may result from the frequent coexistence of chronic conditions.

Taking these considerations into accounts, Ware et al. have used principal component analysis on the MOS SF-36 data collected from 2,474 subjects from the US general population to derive summary scores for the eight categories shown above. (Ware J E Jr., Kosinski M, Keller SD. SF-36 Physical & Mental Health Summary Scales: A user's manual. Boston, Mass.: The Health Institute, New England Medical Center; 3:1–4:6 (1994)). The Physical Component Summary (PCS) and Mental Component Summary (MCS) provide two reliable, reproducible scores for the physical and mental health, respectively. The PCS and MCS scores are converted to a scale of 0 to 100, in which 50 is the mean for the US population.

This analysis of the MOS data takes into account the range of symptoms seen with the chronic condition and reduces the variability from individual patient differences. Low scores on the PCS indicate substantial limitations in self care, physical, social, and role activities, severe bodily pain, frequent tiredness, and health generally rated as poor, whereas high scores indicate no physical limitations, high energy level, and health generally rated as excellent. Low scores on the MCS indicate frequent psychological distress, substantial social and role disability due to emotional problems, and/or health generally rated as poor, whereas high scores indicate frequent positive affect and absence of psychological distress and limitations in usual social and role activities. Table 2 shows relative PCS and MCS scores for various chronic health conditions as compared to US population normative data. Standard deviation is abbreviated as S.D.

TABLE 2

Comparison of Physical Component Summary (PCS) and Mental Component Summary (MCS) of the MOS SF-36 Questionnaire.

| Norms for US Population | Number of Respondents | Mean PCS Score (sd) | Mean MCS Score (sd) |
|---|---|---|---|
| Females | 1,412 | 49.07 (10.42) | 49.33 (10.32) |
| Males | 1,055 | 51.05 (9.39) | 50.73 (9.57) |
| "Healthy" individuals with no chronic conditions from US population | 465 | 55.26 (5.10) | 53.43 (6.33) |

TABLE 2-continued

Comparison of Physical Component Summary (PCS) and Mental Component Summary (MCS) of the MOS SF-36 Questionnaire.

| Norms for US Population | Number of Respondents | Mean PCS Score (sd) | Mean MCS Score (sd) |
|---|---|---|---|
| Individuals with self-reported depression symptoms | 881 | 47.92 (11.62) | 43.46 (11.42) |
| Individuals with Clinical Depression | 502 | 44.96 (12.05) | 34.84 (12.17) |
| Individuals with Arthritis | 826 | 43.15 (11.62) | 48.81 (11.11) |
| Individuals reporting chronic back pain | 519 | 43.14 (11.56) | 46.88 (11.73) |
| Individuals reporting allergies | 818 | 47.44 (10.81) | 48.23 (10.74) |
| Individuals with dermatitis or chronic skin rash | 214 | 46.88 (11.49) | 46.16 (12.06) |

It has been the experience of the present inventors that many patients with inflammation-related diseases respond with only moderate improvement to dietary programs. Further, this response has been variable, with a large percentage of patients with inflammation-related diseases not responding to dietary changes at all. Pharmaceutical approaches, such as non-steroidal anti-inflammatories or anti-depressants have been used with some success, but many of these drugs carry the risk of undesirable side-effects.

Consequently, there is a need for a dietary supplement and/or medical food that ameliorates at least one of the symptoms, preferably all of the symptoms, of an inflammation-related disease, such as arthritis and inflammatory bowel disease. In particular, there is a need for a dietary supplement and/or medical food that improves both the physical and mental functioning of a person suffering from an inflammation-related disease, such as arthritis and inflammatory bowel disease.

SUMMARY OF THE INVENTION

The present invention provides dietary supplements, medical foods and methods effective to ameliorate at least one of the symptoms, preferably all of the symptoms, of an inflammation-related disease, such as arthritis and inflammatory bowel disease. Preferred dietary supplements and medical foods of the present invention improve both the physical and mental functioning of a person suffering from an inflammation-related disease, such as arthritis and inflammatory bowel disease.

The dietary supplements of the present invention are compounded for the amelioration of an inflammation-related disease and include rosemary, curcumin and at least one component selected from the group consisting of quercetin and rutin. A presently preferred dietary supplement of the invention includes rosemary, curcumin and quercetin. A daily dose of the dietary supplements of the present invention include rosemary in an amount of from about 180 mg to about 220 mg; curcumin in an amount of from about 360 mg to about 440 mg; quercetin, if utilized, in an amount of from about 360 mg to about 440 mg; and rutin, if utilized, in an amount of about 360 mg to about 440 mg.

Additionally, presently preferred dietary supplements of the invention may include at least one component selected from the group consisting of limonene, preferably D-limonene, hesperidin and ginger. A daily dose of the dietary supplements of the present invention include limonene, if utilized, in an amount of from about 180 mg to about 220 mg; hesperidin, if utilized, in an amount of from about 360 mg to about 440 mg; and ginger, if utilized, in an amount of from about 180 mg to about 220 mg. The dietary supplements of the present invention optionally include at least one vitamin and at least one non-vitamin antioxidant.

The present invention also provides medical foods comprising rosemary, at least one macronutrient selected from the group consisting of protein, carbohydrate and fat, and at least one member of the group consisting of quercetin, curcumin and rutin, the medical food being compounded for the amelioration of an inflammation-related disease. A daily dose of the medical foods of the present invention include rosemary in an amount of from about 180 mg to about 220 mg; curcumin, if utilized, in an amount of from about 360 mg to about 440 mg; quercetin, if utilized, in an amount of from about 360 mg to about 440 mg; and rutin, if utilized, in an amount of about 360 mg to about 440 mg.

Additionally, presently preferred medical foods of the invention may include at least one component selected from the group consisting of limonene, preferably D-limonene, hesperidin and ginger. A daily dose of the medical foods of the present invention include limonene, if utilized, in an amount of from about 180 mg to about 220 mg; hesperidin, if utilized, in an amount of from about 360 mg to about 440 mg; and ginger, if utilized, in an amount of from about 180 mg to about 220 mg. The medical foods of the present invention optionally include at least one vitamin and at least one non-vitamin antioxidant.

The medical foods of the present invention also include macronutrients. Macronutrients included in the medical foods of the present invention include protein, carbohydrates and fat. The protein is preferably obtained from a cereal grain that is gluten-free, or substantially gluten-free. The presently preferred protein source is a hypoallergenic rice protein concentrate, suitably prepared as disclosed in U.S. patent Ser. No. 4,876,096, incorporated herein by reference. A daily dose of the medical foods of the present invention include protein in an amount of from about 25 g to about 35 g. Carbohydrates are provided as rice fiber, bran and/or flour, or equivalent gluten-free or substantially gluten-free grain fiber, bran and/or flour. Carbohydrate can also be provided as rice syrup solids which contain approximately 70 to 90 percent by weight of high molecular weight dextran, or as equivalent gluten-free or substantially gluten-free grain syrup solids. A daily dose of the medical foods of the present invention include carbohydrate in an amount of from about 43 g to about 69 g. Fats are preferably provided as medium chain triglycerides, preferably in combination with canola oil. Canola oil can be substituted with nutritionally equivalent oils, such as flaxseed oil and safflower oil. Medium chain triglycerides useful in the compositions of the present invention include a fatty acid moiety having an 8 to 14 carbon atom backbone, and can be derived from, for example, coconut oil and related tropical oils. A daily dose of the medical foods of the present invention include fats in an amount of from about 3 g to about 8 g.

Presently preferred medical foods of the invention may also include at least one vitamin, or vitamin precursor. Preferred vitamins possess antioxidant properties and include vitamins A, C and E, and/or their biochemical precursors. Presently preferred medical foods of the invention also include at least one trace element, preferably selected from the group consisting of zinc, manganese and selenium. Presently preferred medical foods of the invention also may include at least one additional antioxidant selected from the group consisting of carotenoids, N-acetylcysteine and L-glutamine. The presently preferred amounts of preferred vitamins, trace elements, non-vitamin antioxidants and other components that can be included in the medical foods of the invention are set forth in Table 3.

In addition, the present invention provides methods for treating inflammation-related diseases. In one embodiment, the methods of the present invention include the step of administering to a person suffering from an inflammation-related disease an effective amount of a dietary supplement of the present invention. Preferably the dietary supplement is administered at least once per day. In another embodiment, the methods of the present invention include the step of administering to a person suffering from an inflammation-related disease an effective amount of a medical food of the present invention. Preferably the medical food is administered at least once per day.

DETAILED DESCRIPTION OF THE PREFERRED EMBODIMENT

The present invention provides dietary supplements, medical foods and methods effective to ameliorate at least one of the symptoms of an inflammation-related disease. Preferred dietary supplements and medical foods of the present invention improve both the physical and mental functioning of a person suffering from an inflammation-related disease. As used herein, the term "inflammation-related disease" refers to a disease for which inflammation is a predominant symptom. By way of non-limiting example, the term "inflammation-related disease" includes arthritis (including osteoarthritis and rheumatoid arthritis), inflammatory bowel disease, eczema, psoriasis, atopic dermatitis, psoriatic arthropathy and asthma.

The compositions of the present invention include rosemary, curcumin (always present in the dietary supplements and optionally present in the medical foods) and at least one component selected from the group consisting of quercetin and rutin. Preferably rosemary is utilized as an extract of ground rosemary leaves; curcumin is utilized as a tumeric extract in powder form; quercetin is utilized as either pure quercetin or as a quercetin glycoside (e.g., rutin). The dietary supplements of the present invention may preferably include ginger, limonene and hesperidin. Ginger is preferably utilized as a concentrate of a ginger root extract. Any substantially pure preparation of limonene or hesperidin can be utilized in the compositions of the present invention.

Rosemary contains the flavonoids carnosol, carnosic acid, rosmanol and ursolic acid and the compositions of the present invention can be supplemented with one or more of the foregoing flavonoids. Ginger contains the potent antioxidant 6-gingerol, together with zingerone and 6-shogaol. The compositions of the present invention can be supplemented with one or more of the foregoing ginger components.

The present invention also provides medical foods comprising rosemary, at least one macronutrient selected from the group consisting of protein, carbohydrate and fat, and at least one member of the group consisting of quercetin, curcumin and rutin, the medical food being compounded for the amelioration of an inflammation-related disease. The protein source is preferably a hypoallergenic rice protein extract, suitably prepared as described in U.S. patent Ser. No. 4,876,096, incorporated herein by reference. The hypoallergenic rice protein extract is preferably fortified with at least one of the following amino acids: L-lysine, L-threonine and L-cysteine. In a presently preferred embodiment, the medical foods of the present invention are fortified with L-lysine and L-threonine in amounts of 6.3% and 0.28% of the weight of rice protein, respectively.

Both the dietary supplements and medical foods of the present invention are preferably used in powder form which can be dissolved in a liquid suitable for human consumption, such as water or a fruit juice. The dietary supplements and medical foods of the present invention can, however, be utilized in any suitable form, such as a solid bar, as a paste, gel, tablet, capsule or liquid.

Typically, the dietary supplements and medical foods of the present invention are preferably administered two times per day, preferably once in the morning and once in the afternoon. A typical treatment regime for the dietary supplements or medical foods will continue for four to eight weeks. Depending on such factors as the medical condition being treated and the response of the patient, the treatment regime may be extended. A medical food of the present invention will typically be consumed in two servings per day as either a meal replacement or as a snack between meals. A serving size for a medical food of the present invention will preferably be in the range of from about 45 grams to about 60 grams and will provide from about 180 calories to about 220 calories to the consumer. In a presently preferred treatment regime a person in need of treatment is provided with two servings of a medical food of the present invention per day. A presently preferred serving size is about 52 grams of powdered medical food which delivers about 200 calories to the consumer.

Suitable ranges for each component preferably included in a medical food in accordance with the present invention are set forth in Table 3 of Example 1. For a dietary supplement compounded in accordance with the present invention, the same ranges of specific ingredients to be included (e.g. Rosemary, Curcurmin, Quercetin, etc.) are utilized. The following examples merely illustrate a preferred embodiment now contemplated for practicing the invention, but should not be construed to limit the invention.

EXAMPLE 1

Improvement in PCS and MCS Components of the MOS SF-36 in Patients Treated with a Preferred Medical Food of the Present Invention Control Subjects: Sixteen subjects were included in the control, no-intervention study. These subjects were asked to complete a MOS questionnaire at the beginning of the study, and subsequently after an interval of between 1 to 15 weeks. Subjects were told to maintain their routines of diet, medication, and lifestyle and make no intentional changes in the intervening time. The control subjects varied in age from 39 to 61 years, with an average age of 49±7 years, and included 4 men and 12 women.

Subjects with inflammation-related conditions: Fourteen patients with primary symptoms relating to chronic inflammation were evaluated with the intervention protocol for response. Subjects varied in age from 16 to 55 years, with an average age of 43±11 years, and included 5 men and 12 females.

Intervention Protocol: Control subjects received no intervention. Nutritional intervention for the subjects with inflammation-related disease involved supplementation of the daily diet with a presently preferred medical food of the invention described in Table 3 (Composition 1). Composition 1 was manufactured as a powdered drink mix, which was prepared by each subject at the time of use by mixing the appropriate amount of the composition in either water or a juice of the subject's choosing. Composition 1 was delivered in two servings per day of 52-gram size, which delivered 400 calories per day to the diet.

Intervention Protocol with Clinical Assessment: Subjects on the intervention protocols were provided with Composition 1 in a powdered form and a dietary protocol. The dietary changes prescribed in the dietary protocol consisted of a modified elimination diet, which is described as a diet free of substances known to produce allergenic responses and is preferably vegetarian. Subjects were instructed to make no changes in supplementation, medication, or exercise routine during the course of the intervention. Medications consumed by the subjects were documented at each office visit. Likewise, compliance to the protocol during the previous weeks was documented by questionnaire during the office visit.

Subjects were maintained on the protocol for between four and nine weeks. Subjects were evaluated by the MOS SF-36 questionnaire, a condition-specific questionnaire when appropriate, and a questionnaire to evaluate general physical symptoms called the Medical Symptoms Questionnaire (MSQ), described in Bland, J. S., and Bralley, J. A., Journal of Applied Nutrition 44: 2–15 (1992). Data were analyzed by standard statistical methods.

TABLE 3

Weight ranges for components of medical food of the invention and composition of presently preferred medical food of the invention (Composition 1).

| Nutrient | Units | Amount per day in medical food of the present invention | |
|---|---|---|---|
| | | Composition 1 | Range |
| Rice protein | grams | 30 | 25–35 |
| Rice fiber | grams | 8 | 7–9 |
| Rice carbohydrates | grams | 48 | 43–53 |
| Vegetable Oil | grams | 3.34 | 3–4 |
| Medium-chain tryglycerides | grams | 3.34 | 3–4 |
| Vitamin A (mixed carotenoids/palmitate) | IU | 10,000 | 9,000–11,000 |
| Vitamin C | mg | 360 | 320–400 |
| Calcium | mg | 550 | 500–600 |
| Vitamin D | IU | 200 | 180–220 |
| Vitamin E | IU | 200 | 180–220 |
| Thiamin (B1) | mg | 4 | 3–5 |
| Riboflavin (B2) | mg | 4 | 3–5 |
| Niacin (B3) | mg | 70 | 60–80 |
| Vitamin B6 | mg | 10 | 8–12 |
| Folic acid | μg | 160 | 140–180 |
| Vitamin B12 | mcg | 6 | 5–7 |
| Biotin | mcg | 300 | 270–330 |
| Pantothenic Acid | mg | 10 | 8–12 |
| Phosphorous | mg | 400 | 360–440 |
| Magnesium | mg | 560 | 500–600 |
| Zinc | mg | 20 | 18–22 |
| Selenium | mcg | 150 | 140–160 |
| Copper | mg | 2 | 1.5–2.5 |
| Manganese | mg | 4 | 3.5–4.5 |
| Chromium | mcg | 120 | 100–140 |
| N-acetyl cysteine (NAC) | mg | 200 | 180–220 |
| Sodium sulfate | mg | 100 | 80–120 |
| Molybdenum | mcg | 76 | 65–85 |
| L-glutamine | mg | 1500 | 1200–1800 |
| L-threonine | mg | 68 | 60–75 |
| L-lysine HCl | mg | 1540 | 1200–1800 |
| Citrulline | mg | 200 | 180–220 |
| Hesperidin | mg | 400 | 360–440 |
| Quercetin | mg | 400 | 360–440 |
| Rutin | mg | 400 | 360–440 |
| Curcumin | mg | 400 | 360–440 |
| Rosemary | mg | 200 | 180–220 |
| D-limonene | mg | 200 | 180–220 |
| Ginger | mg | 200 | 180–220 |

Changes with no intervention: The changes in MOS SF-36 responses was evaluated over time with no intervention. In Table 4, the average change in score in the eight MOS categories is seen to be seven or less points in the 16 control subjects. In Table 5, the summary PCS and MCS scores for the control subjects are shown, which also reveal that the summary scores remain consistent over the course of 4±3 weeks.

TABLE 4

Summary of the Eight Categories of the SF-36 in 16 Subjects With no Intervention (Average Intervening Time Between Initial Score and Final Score Was 4 ± 3 Weeks).

|  | Initial Score | Final Score | Average Change in Score |
|---|---|---|---|
| Physical Functioning | 60 ± 30 | 64 ± 32 | −4 ± 17 |
| Role-Physical | 41 ± 39 | 44 ± 40 | −3 ± 38 |
| Bodily Pain | 55 ± 21 | 50 ± 26 | 5 ± 21 |
| General Health | 54 ± 24 | 50 ± 21 | 4 ± 16 |
| Vitality | 31 ± 19 | 38 ± 15 | −7 ± 11 |
| Social Function | 66 ± 27 | 62 ± 24 | 4 ± 26 |
| Role-Emotional | 53 ± 43 | 51 ± 43 | 2 ± 42 |
| Mental Health | 60 ± 20 | 64 ± 11 | −4 ± 18 |

TABLE 5

Physical Component Summary (PCS) and Mental Component Summary (MCS) Scores From the MOS SF-36 in 16 Subjects With no Intervention (Average Intervening Time Was 4 ± 3 Weeks).

|  | Physical Component Summary (PCS) | | | Mental Component Summary (MCS) | | |
|---|---|---|---|---|---|---|
|  | Initial Score | Final Score | Change | Initial Score | Final Score | Change |
| Average (sd) | 39 ± 11 | 39 ± 13 | 0.34 ± 7.9 | 43 ± 13 | 42 ± 8.4 | 0.51 ± 9.9 |

Data obtained from 14 subjects with inflammation-related conditions who received the nutritional intervention are shown below. In Table 6, the average change per individual category of the MOS SF-36 is shown. In Table 7, the primary complaint(s) and weeks on the protocol are shown, as well as the PCS and MCS scores.

After intervention with Composition 1, the majority of subjects reported improvement in the physical parameters of the MOS SF-36, as shown by the increase in scores in the Physical Functioning, Role Physical, Bodily Pain, and General Health sections. The increase in scores for the majority of patients is reflected in the Physical Component Summary score, shown in Table 7. Two patients reported significant increase in symptoms, although both patients showed considerable improvement on the Mental Component Summary scores. Without these two subjects included, the average improvement in PCS is 5 points.

TABLE 6

Summary of the 8 Categories of the MOS SF-36 in 14 Subjects With Inflammation-Related Conditions

|  | Initial Score | Final Score | Average Change in Score |
|---|---|---|---|
| Physical Functioning | 69 ± 32 | 75 ± 33 | 6 ± 15 |
| Role-Physical | 46 ± 43 | 59 ± 43 | 13 ± 29 |
| Bodily pain | 52 ± 28 | 67 ± 31 | 15 ± 21 |
| General Health | 47 ± 17 | 59 ± 24 | 12 ± 13 |
| Vitality | 46 ± 20 | 57 ± 21 | 11 ± 19 |
| Social Function | 63 ± 31 | 70 ± 26 | 7 ± 39 |
| Role-Emotional | 64 ± 46 | 90 ± 20 | 26 ± 57 |
| Mental Health | 70 ± 15 | 79 ± 13 | 9 ± 14 |

TABLE 7

The Physical Component Summary (PCS) and Mental Component Summary (MCS) from 14 Subjects with Inflammation-Related Conditions Before and After Intervention with Composition 1.

| Patient Code | Major Symptoms | Weeks | Physical Component Summary (PCS) | | | Mental Component Summary (MCS) | | |
|---|---|---|---|---|---|---|---|---|
|  |  |  | Initial Score | Final Score | Change | Initial Score | Final Score | Change |
| 421 | Rheumatoid arthritis | 3 | 32 | 19 | −13 | 48 | 58 | 10 |
| 395 | Rheumatoid arthritis | 6 | 33 | 52 | 20 | 59 | 46 | −13 |
| 235 | Rheumatoid arthritis | 7 | 50 | 53 | 2.8 | 47 | 55 | 8.1 |
| 298 | Rheumatoid arthritis | 7 | 13 | 15 | 2.5 | 62 | 58 | −3.3 |
| 370 | Rheumatoid arthritis | 9 | 45 | 54 | 9.1 | 21 | 52 | 32 |
| 170 | Psoriatic arthritis | 8 | 18 | 12 | −6.0 | 60 | 67 | 6.4 |
| 299 | Asthma | 9 | 43 | 39 | −3.9 | 34 | 47 | 13 |
| 389 | Chronic urticaria | 9 | 40 | 40 | 0.0 | 31 | 45 | 14 |
| 134 | Colitis | 8 | 36 | 39 | 2.8 | 42 | 52 | 10 |
| 430 | Inflammatory bowel disease | 9 | 55 | 57 | 1.9 | 52 | 57 | 4.8 |

TABLE 7-continued

The Physical Component Summary (PCS) and Mental Component Summary (MCS) from 14 Subjects with Inflammation-Related Conditions Before and After Intervention with Composition 1.

| Patient Code | Major Symptoms | Weeks | Physical Component Summary (PCS) | | | Mental Component Summary (MCS) | | |
|---|---|---|---|---|---|---|---|---|
| | | | Initial Score | Final Score | Change | Initial Score | Final Score | Change |
| 52 | Inflammatory bowel disease | 9 | 41 | 57 | 16 | 54 | 43 | −11 |
| 571 | Inflammatory bowel disease | 8 | 40 | 49 | 8.9 | 49 | 42 | −6.9 |
| 462 | Inflammatory bowel disease | 5 | 29 | 35 | 6.2 | 46 | 49 | 2.7 |
| 41 | Inflammatory bowel disease | 7 | 49 | 51 | 1.6 | 33 | 59 | 26 |
| 44 | Inflammatory bowel disease | 10 | 56 | 38 | −18 | 54 | 59 | 5.0 |
| Ave (Sd) | | 8 ± 2 | 39 ± 13 | 41 ± 15 | 2.0 ± 10 | 46 ± 12 | 53 ± 7.4 | 6.3 ± 13 |

EXAMPLE 2

Antioxidant Properties of Curcumin, Quercetin and Rosemary

In the inflammatory state, the potential for a positive feed-back loop exists in oxidative stress induces the production of cytokines which then have the potential to increase the risk of further oxidative damage (Reilly, M P et at, J. Nutr. 128: 434S-438S Conner, E M et al, Nutrition 12:274–277 (1996); Baeurle, P A and T Henkel, Annu. rev. Immunol. 12: 141–179(1994); Weiss, S J, New England J Med. 320: 365–376 (1989). One method of interrupting this vicious circle involves the use of antioxidants (Jacob, R A, Nutr. Res. 15: 755–766 (1995); Halliwell, B, Nutr. Rev. 52: 253–265(1994); Suzuki, Y J et al, Biochem. Biophys. Res. Commun. 189: 1709–1715(1992)). Several phytonutrients possessing antioxidant activity have been utilized in an attempt to intervene in this cyclic process (Sato, M et al, J. Rheumatology 24: 1680–1684 (1997); Skaper, S D et al, Free Radical Biol. Med. 22: 669–678 (1997); Shoskes, D A, Transplantation. 66: 147–152 (1998); Chan, M M et al, Canc. Lett. 96:23–29 (1995)).

Bioflavonoids, such as quercetin (Rice-Evans, C A et al, Free Radical Biol. Med. 20: 933–956 (1996), ferulic acid-derivatives such as curcumin (Sreejayan, N and MNA Rao, Arzneim. Forsch./Drug Res. 46: 169–171(1996) and camosic acid derivatives from rosemary (Richheimer, S L et al, JAOCS 73: 507–514 (1996) have all been demonstrated to possess potent antioxidant activity in vitro which is reflected in their clinical applications. The present example demonstrates the synergistic antioxidant activity of components of the dietary supplements and medical foods of the present invention.

Free radicals are defined as "any [molecular] species capable of independent existence that contains one or more unpaired electrons." (Halliwell D, Gutteridge J M C. *Free Radicals in Biology and Medicine.* 2nd ed. Oxford: Clarendon Press; pp. 10–14, (1989)). The tendency to fill molecular or atomic orbitals by forming electron pairs is the basis of free radical reactivity. The reactive nature of oxygen containing free radicals explains their tendency to destroy biological molecules.

Perhaps the classic example of free radical damage is that of lipid peroxidation. The reaction can be initiated by hydroxyl radical generated by the reaction of ferrous ion with hydrogen peroxide (Fenton reaction) summarized below. The loss of an electron (accompanied by proton, $H^+$) by the lipid (LH), a typical oxidation reaction, produces a second radical (L.) as one of the reaction products:

$LH + .OH \rightarrow L. + H_2O$ (chain initiation by .OH)

$L. + O_2 \rightarrow LOO.$ $LOO. + LH \rightarrow L. + LOOH$ (chain propagation)

It is apparent that without a mechanism to break this chain of events, the reaction could easily spiral out of control. In the case of lipid peroxidation, the reactions of vitamins E and C effectively quench the reaction initiated by a lone hydroxyl radical. Rather than reacting with an additional membrane lipid, an electron is transferred from the lipid peroxyl radical to a nearby tocopherol molecule (E), thus generating the tocopheryl radical. The return of the vitamin to the reduced state is accomplished by reaction with ascorbic acid.

A number of phytonutrients not commonly considered essential for health also have the capacity to quench oxygen radical mediated reactions. Quercetin, curcumin and the rosemary diterpenes, carnosol and carnosic acid have been studied in this regard (Cuvelier, M-E et al., *JAOCS* 73: 645–652 (1996); Richheimer, S L et al. 1996 JAOCS 73: 507–514 (1996); Sreejayan, N and M. N. A. Rao., *Arzneim.-Forsch/Drug Res.* 46: 169–171 (1996); Haenen, G. R. M. M. et al., *Biochem. Biophys. Res. Comm.*, 236: 591–593 (1997); Chan, M. M.-y et al., *Canc. Lett.* 96: 23–29 (1995); Jovanovic, S V et al., *J. Am Chem Soc.* 116: 4846–4851 (1994); Guo, C. et al., *J. Agric. Food Chem.* 45: 1781–1796 (1997); Rice-Evans, C A et al., *Free Rad. Biol. Med* 20: 933–956 (1996).

The results reported in the present example demonstrate that a mixture containing quercetin, curcumin and rosemary extract act synergistically in vitro. That is to say, the antioxidant activity of the mixture is greater than that which would be predicted based on the individual bioactivities.

Method: In order to determine the antioxidant capacity of the subject phytonutrients, the ORAC assay (Cao, G et al., *Free Rad. Biol. Med.* 14: 303–311(1989)) was utilized. This simple procedure relies on the fact that peroxyl radicals will quench the fluorescence of β-phycoerythrin (β-PE) The addition of an antioxidant capable of scavenging these radicals is able to inhibit fluorescence quenching. Fluorescence is monitored as a function of time and the extent of quenching and its inhibition can be determined by calculating the area under the curve (AUC).

A typical reaction will contain $1.67 \times 10^{-8}$ M β-PE in phosphate buffer and $3 \times 10^{-3}$ M 2,2'-azobis(2-amidinopropane)dihydochloride (AAPH) as well as test material. The reaction is initiated by the addition of the peroxyl-radical generating reagent AAPH. Fluorescence ($\lambda_{excit}$=540 nm; $\lambda_{emis}$=565 nm) is measured at one minute intervals and the AUC is determined. The difference, or net protection, is equal to $AUC_{sample} - AUC_{blank}$, and represents the antioxidant capacity of the sample. This difference is compared to a standard sample (1 μM final concentration) of the water soluble vitamin E analog, Trolox, and the result is expressed in ORAC units. Where one ORAC unit (U) is defined as the net protection provided by 1 nmol/ml Trolox (i.e., 1 μM). The reaction shows remarkable linearity for a variety of antioxidants (Cao et al, 1993). The final results are normalized to Trolox on a weight basis.

$$\text{units} = (AUC/\mu g)_{test}/(AUC/\mu g)_{trolox}.$$

To generate the data set forth in the present example, samples were prepared in acetonitrile, sometimes with the aid of sonication to facilitate dissolution. One to five μl of sample was added to each 3 ml cuvette, the reaction initiated with AAPH and fluorescence monitored until the quenching was complete. The predicted value for the mixtures was calculated by using the following equation:

$$U_{pred} = f_q U_q + f_c U_c + f_r U_r$$

where $f_q$, $f_c$ and $f_r$ represent the weight percent and $U_q$, $U_c$, $U_r$ is the activity of the pure ingredient for quercetin, curcumin and rosemary respectively.

Tables 8 and 9 show the antioxidant properties of curcumin, quercetin and rosemary, alone or in combination, as measured using the ORAC assay. The antioxidant properties of pure samples of curcumin, quercetin, rosemary and Trolox were individually assayed and the results are set forth in Table 8. The antioxidant properties of mixtures of curcumin, quercetin and rosemary were assayed and the observed values were compared to the predicted values, as set forth in Table 9. The predicted values were determined by adding the individually determined values (set forth in Table 8) for each of the components of the mixture. The observed values were greater than the predicted values for each combination of: rosemary plus curcumin; rosemary plus quercetin, and rosemary plus curcumin and quercetin. These data demonstrate that rosemary interacts synergistically with curcumin and quercetin in the in vitro ORAC assay. Additionally, as shown in Table 9, this synergistic effect was also observed when Composition 1 (having the composition set forth in Table 3) was assayed using the ORAC assay.

TABLE 8

ORAC Activity of Pure Samples of Curcumin, Quercetin, Rosemary and Trolox

| Percent of Sample Tested (by weight) | | | | AUC/μg | | ORAC |
|---|---|---|---|---|---|---|
| curcumin | quercetin | rosemary | Trolox | mean | sd | units (U) |
| 100% | | | | 15.93 | 3.7 | 1.79 |
| | 100% | | | 14.45 | 1.67 | 1.62 |
| | | 100% | | 4.79 | 1.14 | 0.54 |
| | | | 100% | 8.9 | 1.45 | 1.00 |

TABLE 9

ORAC activity of combinations of curcumin, quercetin and rosemary

| Grams in Mixture | | | Fraction by Weight | | | AUC/μg | | Units ORAC Unit | |
|---|---|---|---|---|---|---|---|---|---|
| curcumin | quercetin | rosemary | curcumin | quercetin | rosemary | mean | s.d. | pred. | obs. |
| 25.2 | 24.9 | | 0.503 | 0.497 | | 15.47 | 4.82 | 1.71 | 1.74 |
| 33.9 | | 16.1 | 0.678 | | 0.322 | 19.47 | 6.1 | 1.39 | 2.19 |
| | 33.8 | 16.3 | | 0.675 | 0.325 | 15.68 | 8.72 | 1.27 | 1.76 |
| 20.3 | 9.7 | 20.1 | 0.405 | 0.194 | 0.401 | 21.02 | 1.33 | 1.26 | 2.36 |
| Composition 1 | | | 0.004 | 0.004 | 0.002 | 1.27 | 3.17 | 0.01 | 0.05 |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for treating an inflammation disease comprising administering to a person suffering from an inflammation disease a synergistically effective amount of a dietary supplement comprising rosemary, quercentin, and curcumin;
    wherein the ratio of rosemary to quercetin ranges from about 2:1 to about 1:2; and
    wherein the ratio of rosemary to curcumin ranges from about 1:1 to about 1:2.

2. The method of claim 1 wherein the dietary supplement further comprises limonene, hesperidin and ginger.

3. The method of claim 1, wherein the quercetin is in the form of rutin.

4. A method for treating an inflammation disease comprising administering to a person suffering from an inflammation disease a synergistcally effective amount of a medical food comprising rosemary, quercetin, and curcumin at least one macronutrient selected from the group consisting of protein, carbohydrate, and fat,
    wherein the ratio of rosemary to quercetin ranges from about 2:1 to about 1:2 and
    wherein the ratio of rosemary to curcumin ranges from about 1:1 to about 1:2.

5. The method of claim 4 wherein the medical food further comprises limonene, hesperidin and ginger.

6. The method of claim 4 wherein the protein is a hypoallergenic rice protein.

7. The method of claim 4, wherein the quercetin is in the form of rutin.

* * * * *